(12) United States Patent
Samei

(10) Patent No.: US 11,968,341 B2
(45) Date of Patent: Apr. 23, 2024

(54) IMAGE READING DEVICE, IMAGE FORMING APPARATUS, AND FEED TRAY COMPRISING A STERILIZING LIGHT SOURCE TO STERILIZE A SHEET

(71) Applicant: Masahiro Samei, Kanagawa (JP)

(72) Inventor: Masahiro Samei, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 17/725,883

(22) Filed: Apr. 21, 2022

(65) Prior Publication Data

US 2022/0377197 A1  Nov. 24, 2022

(30) Foreign Application Priority Data

May 18, 2021 (JP) ................................. 2021-083976

(51) Int. Cl.
*A61L 2/10* (2006.01)
*A61L 2/26* (2006.01)
*H04N 1/00* (2006.01)

(52) U.S. Cl.
CPC ............ *H04N 1/00997* (2013.01); *A61L 2/10* (2013.01); *A61L 2/26* (2013.01); *H04N 1/00822* (2013.01); *A61L 2202/11* (2013.01); *A61L 2202/26* (2013.01)

(58) Field of Classification Search
CPC .......... A61L 2/10; A61L 2/26; A61L 2202/11; A61L 2202/26; H04N 1/00997; H04N 1/00822

USPC ........................................ 358/471, 1.11–1.18
See application file for complete search history.

(56) References Cited

U.S. PATENT DOCUMENTS

| 5,975,515 A | * | 11/1999 | Capri ................. G03G 15/6502 |
| | | | 271/145 |
| 2012/0086958 A1 | * | 4/2012 | Srnka .................... G06F 3/1271 |
| | | | 358/1.6 |
| 2015/0220028 A1 | | 8/2015 | Samei et al. |
| 2015/0220029 A1 | | 8/2015 | Samei et al. |
| 2018/0067417 A1 | * | 3/2018 | Iino ...................... B41J 11/0021 |
| 2022/0152238 A1 | * | 5/2022 | Nakashita .......... H04N 1/00503 |
| 2022/0296755 A1 | * | 9/2022 | Wurmfeld ................. A61L 2/10 |

FOREIGN PATENT DOCUMENTS

| CN | 212677227 U | * | 3/2021 |
| JP | 4-256414 | | 9/1992 |
| JP | 2004-215162 | | 7/2004 |
| JP | 2005115268 A | * | 4/2005 |
| JP | 2005218850 A | * | 8/2005 |
| JP | 2014-109645 | | 6/2014 |

(Continued)

*Primary Examiner* — Chad Dickerson
(74) *Attorney, Agent, or Firm* — Duft & Bornsen, PC

(57) ABSTRACT

An image reading device, an image forming apparatus, and a feed tray. The image reading device is provided with a light source that irradiates a sheet with light, and the light source is a sterilizing-light emitting light source that irradiates the sheet with light to sterilize the sheet. The image forming apparatus includes the image reading device, a housing including an image forming device that forms an image on a sheet, and a sterilizing-light emitting light source disposed in a sheet conveyance path in the housing. The feed tray for containing a plurality of sheets, the feed tray includes a sterilizing-light emitting light source.

4 Claims, 3 Drawing Sheets

(56) References Cited

FOREIGN PATENT DOCUMENTS

| | | | |
|---|---|---|---|
| JP | 2014-110495 | | 6/2014 |
| JP | 2014109645 A | * | 6/2014 |
| JP | 2017228883 A | * | 12/2017 |
| JP | 2018007929 A | * | 1/2018 |
| KR | 20200042186 A | * | 10/2018 |

* cited by examiner

IMAGE READING DEVICE, IMAGE FORMING APPARATUS, AND FEED TRAY COMPRISING A STERILIZING LIGHT SOURCE TO STERILIZE A SHEET

CROSS-REFERENCE TO RELATED APPLICATION

This patent application is based on and claims priority pursuant to 35 U.S.C. § 119(a) to Japanese Patent Application No. 2021-083976, filed on May 18, 2021, in the Japan Patent Office, the entire disclosure of which is hereby incorporated by reference herein.

BACKGROUND

Technical Field

Embodiments of the present disclosure relate to an image reading device, an image forming apparatus, and a feed tray.

Background Art

In the related art, an image reading device provided with a light source configured to irradiate a document with light is known in the art. For the purposes of providing a reader capable of sterilizing a document while conveying the document, for example, such a known image reading device may be provided with a light-source lamp for sterilization at some midpoint in the conveyance path of an automatic document feeder (ADF) of a reader.

SUMMARY

Embodiments of the present disclosure described herein provide an image reading device, an image forming apparatus, and a feed tray. The image reading device is provided with a light source that irradiates a sheet with light, and the light source is a sterilizing-light emitting light source that irradiates the sheet with light to sterilize the sheet. The image forming apparatus includes the image reading device, a housing including an image forming device that forms an image on a sheet, and a sterilizing-light emitting light source disposed in a sheet conveyance path in the housing. The feed tray for containing a plurality of sheets, the feed tray includes a sterilizing-light emitting light source.

BRIEF DESCRIPTION OF THE DRAWINGS

A more complete appreciation of embodiments and the many attendant advantages thereof will be readily obtained as the same becomes better understood by reference to the following detailed description when considered in connection with the accompanying drawings.

Figure 1:
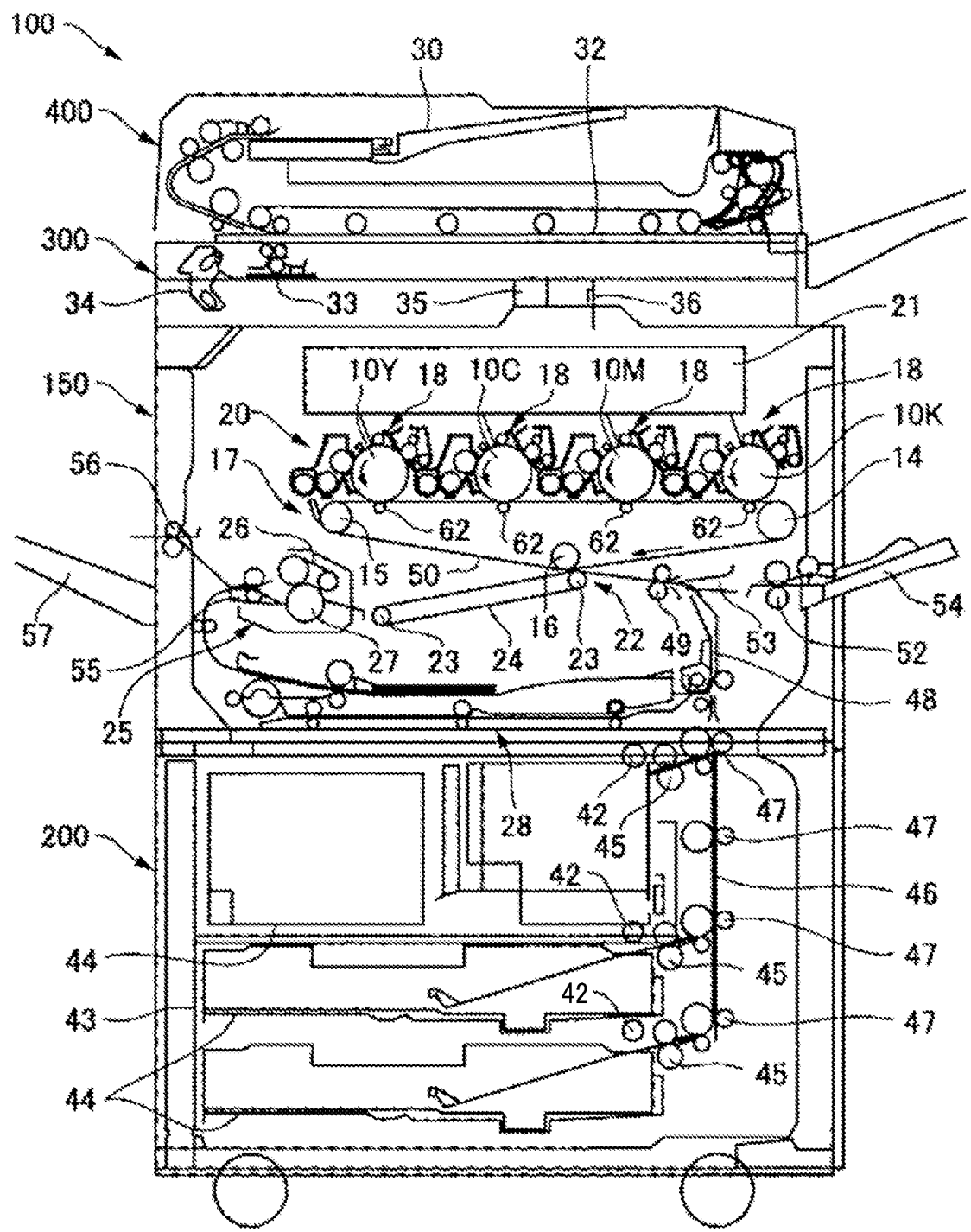
FIG. 1 is a schematic diagram of a color image forming apparatus according to an embodiment of the present disclosure.

The accompanying drawings are intended to depict embodiments of the present disclosure and should not be interpreted to limit the scope thereof. The accompanying drawings are not to be considered as drawn to scale unless explicitly noted.

DETAILED DESCRIPTION

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the present disclosure is not intended to be limited to the specific terminology so selected and it is to be understood that each specific element includes all technical equivalents that have the same structure, operate in a similar manner, and achieve a similar result.

A document reading device according to an embodiment of the present disclosure may be provided for an image forming apparatus as follows. Such an image forming apparatus includes at least an electrostatic latent image carrier, an electrostatic latent image forming unit used to form an electrostatic latent image on the electrostatic latent image carrier, a developing unit configured to develop the electrostatic latent image with toner to form a visible image, transfer means configured to transfer the visible image onto a recording medium, and a fixing device configured to fix the image transferred onto the recording medium. Further, such an image forming apparatus may include any desired means or unit such as an electric-electric-charge removing bias, a cleaner, a recycling unit, and a controller where appropriate Such a recording method as above may be applied to an image forming apparatus using other kinds of methods such as inkjet recording mode in place of the image forming apparatus using the electrophotographic method. Such a recording mode as above may also be applied to a discrete unit of image reading device. An electrophotographic image forming apparatuses according to an embodiment of the present disclosure is described below.

For example, the material, the shape, the structure, and the size of an electrostatic latent image carrier, which may be referred to as an electrophotographic photoconductor or may be referred to simply as a photoconductor, is not limited to any particular embodiment, and may be selected from any desired known material, shape, or structure as appropriate. Preferably, an electrostatic latent image carrier has a drum-like shape, and the material of an electrostatic latent image carrier may be, for example, an inorganic photoconductor such as amorphous silicon (Si) and selenium or an organic photoconductor (OPC) such as polysilane, phthalopolymethine, and phthalocyanine.

For example, an electrostatic latent image forming unit can evenly charge the surface of the electrostatic latent image carrier, and then can perform exposures according to the shape of the image. As a result, an electrostatic latent image can be formed. For example, an electrostatic latent image forming unit is provided with, at least, a charger that evenly charges the surface of the electrostatic latent image carrier and an exposure device that exposes the surface of the latent image carrier according to the shape of the image.

For example, a charger may be used to apply a voltage to the surface of the electrostatic latent image carrier. As a result, electrical charge can be implemented. Such a charger is not limited to any particular embodiment, and any desired charger may be adopted depending on the intended purpose. For example, a known contact charger provided with, for example, a conductive or semiconductive roller, a brush, a film, and a rubber blade, or a non-contact charger such as a corotron and a scorotron that makes use of corona discharge may be adopted.

It is desired that the charger be arranged near the electrostatic latent image carrier in a condition of contact or condition of non-contact to charge the surface of the electrostatic latent image carrier. Such an electrical charge is implemented by applying a direct current or an alternating voltage to the electrostatic latent image carrier in an overlapping manner. It is desired that the charger be a charging roller arranged near the electrostatic latent image carrier in a non-contact manner through a gap seal tape. Preferably, the charger applies a direct current or an alternating voltage to the charging roller in an overlapping manner to charge the surface of the electrostatic latent image carrier.

For example, an exposure device may be used to expose the surface of the electrostatic latent image carrier according to the shape of the image. As a result, exposure can be implemented. The exposure device is not limited to any particular embodiment, and any desired exposure device may be selected depending on the intended purpose as long as it can perform exposure to form an image as desired on the surface of the electrostatic latent image carrier that is charged by the charger. For example, various kinds of exposure devices such as a copying optical system, a rod lens array system, a laser optical system, and a liquid crystal shutter optical system may be adopted. In the present embodiment, a backlighting method or system may be adopted in which exposure is performed from the rear side of the electrostatic latent image carrier to form an image as desired.

The formation of a visible image can be carried out, for example, by developing an electrostatic latent image with the toner according to the present embodiment, and can be carried out by a developing unit. The developing unit is not limited to any particular embodiment, and may be selected from any known developing devices as long as development can be performed using toner. For example, it is desired that the developing unit contain toner and have at least a developing device capable of applying the developer to an electrostatic latent image in a contact or non-contact manner. More preferably, the developing device is provided with a container that contains toner.

The transfer of a visible image can be performed, for example, by charging an electrostatic latent image carrier or photoconductor using a transfer charger, and can be performed by a transfer means. Preferably, the transfer means according to the present embodiment includes a primary transfer unit that transfers a visible image onto an intermediate transferor to form a composite transfer image, and a secondary transfer unit that transfers the composite transfer image onto a recording medium. The intermediate transferor is not limited to any particular embodiment, and any desired known transferor such as a transfer belt may be adopted depending on the intended purpose.

Preferably, the transfer means provided with the primary transfer unit and secondary transfer unit has at least a transfer unit that separates and charges the visible image formed on the electrostatic latent image carrier or the photoconductor to the recording medium side. The number of transfer means may be one or two or more. The transfer unit according to the present embodiment may be, for example, a corona transfer device that uses corona discharge, a transfer belt, a transfer roller, a pressure transfer roller, and an adhesion transfer device. The recording medium is not limited to any particular embodiment, and any desired known recording medium or recording sheet may be adopted where appropriate.

Such a fixing device is not limited to any particular embodiment, and any desired charger may be adopted depending on the intended purpose. Preferably, a known heating and pressurizing unit is used as the fixing device. The heating and pressing unit according to the present embodiment include, for example, a combination of a heating roller and a pressure roller, and a combination of a heating roller, a pressure roller, and an endless belt.

The electric-charge removing unit according to the present embodiment is not limited to any particular embodiment. As long as an electric-charge removing bias can be applied to the electrostatic latent image carrier, any desired known discharger may be adopted where appropriate. Preferably, an electric-charge removing lamp or the like may be adopted.

The cleaner according to the present embodiment is not limited to any particular embodiment. As long as the toner remaining on the electrostatic latent image carrier can be removed, any desired known cleaner may be adopted where appropriate. Preferably, for example, a magnetic brush cleaner, an electrostatic brush cleaner, a magnetic roller cleaner, a blade cleaner, a brush cleaner, and a web cleaner may be adopted as the cleaner.

The controller according to the present embodiment is a means for controlling a plurality of units. The controller according to the present embodiment is not limited to any particular embodiment. As long as the operation or movement of the multiple units can be controlled, any desired controller may be adopted depending on the intended purpose. For example, a device such as a sequencer and a computer or one or more processors may be adopted.

FIG. 1 is a diagram illustrating the internal structure of a color image forming apparatus 100 according to an embodiment of the present disclosure.

Although an electrophotographic photocopier that adopts a tandem indirect transferring method is adopted in the present embodiment, the image forming apparatus 100 according to the present embodiment is not limited to any particular embodiment. In FIG. 1, a photocopier housing 150, a sheet feeding table 200 on which the photocopier housing 150 is placed, an image reading device 300 mounted on the photocopier housing 150, and an automatic document feeder (ADF) 400 mounted on the image reading device 300 are illustrated.

An intermediate transferor 50 that is shaped like an endless belt and extends in the lateral direction is arranged in the center of the photocopier housing 150. In the present embodiment described with reference to FIG. 1, the intermediate transferor 50 is looped around three support rollers 14, 15, and 16 so as to be rotatable in a clockwise direction in FIG. 1. An intermediate transferor cleaner 17 that removes the residual toner remaining on the intermediate transferor 50 after image transfer is disposed on the left side of the second support roller 15 among the three support rollers 14, 15, and 16.

Over the intermediate transferor 50 stretched between the first support roller 14 and the second support roller 15 out of the three support rollers, four image forming devices 18 for yellow (Y), cyan (C), magenta (M), and black (BK) toner are arranged side by side in the direction of conveyance to form a tandem image forming unit 20. In the tandem image forming unit 20 according to the present embodiment, each one of the image forming device 18 is provided with a charger, a developing device, a primary transfer device 62, an electric-charge removing device around a photoconductor 10 shaped like a drum.

An exposure device 21 is arranged directly above the tandem image forming unit 20. On the other hand, a secondary transfer device 22 is disposed on the other side of the tandem image forming unit 20 across the intermediate transferor 50.

In the present embodiment described with reference to FIG. 1, the secondary transfer device 22 is configured such that a secondary transfer belt 24, which is an endless belt, is looped around a pair of rollers 23. The secondary transfer device 22 is arranged so as to be pressed against the third support roller 16 through the intermediate transferor 50, and transfers an image on the intermediate transferor 50 to a sheet. A fixing device 25 is disposed downstream from the secondary transfer device 22 in the direction of conveyance of a sheet. In FIG. 1, the fixing device 25 is disposed on the left side of the secondary transfer device 22. The fixing device 25 receives the sheet that bears a color toner image, and fixes the color toner image onto the sheet.

The fixing device 25 includes a fixing belt 26 and a pressure roller 27. The pressure roller 27 is pressed against the fixing belt 26 that is an endless belt. The above-described secondary transfer device 22 also has a sheet conveying function of conveying the sheet after image transfer to the fixing device 25. In the present embodiment described with reference to FIG. 1, a sheet reversing device 28 is disposed parallel to the tandem image forming unit 20 below the above secondary transfer device 22 and fixing device 25. The sheet reversing device 28 reverses a sheet such that duplex printing will be performed to print another toner image on the reverse side of the sheet. In the present embodiment described with reference to FIG. 1, a manual feed tray 54, and a conveyance roller 52 and a conveyance path 53 to be used for the sheets manually fed from the manual feed tray 54 are also arranged.

The sheet feeding table 200 is a sheet feeding table on which the photocopier housing 150 is placed. A plurality of feed trays 44 are arranged in layers in a sheet bank 43. In FIG. 1, three feed trays 44 are stored in the sheet bank 43 in layers. A sheet feeding roller 42 and a separation roller pair 45 are provided for each one of the multiple feed trays 44. A plurality of conveyance rollers 47 are arranged in a sheet conveyance path 46 running inside the sheet feeding table 200.

The image reading device 300 according to the present embodiment is provided with, for example, a contact glass 32, a first carrier 33, a second carrier 34, an imaging lens 35, and a sensor 36.

An automatic document feeder (ADF) 400 is provided with a sheet tray 30 and a sheet feeding mechanism.

Figure 2A:
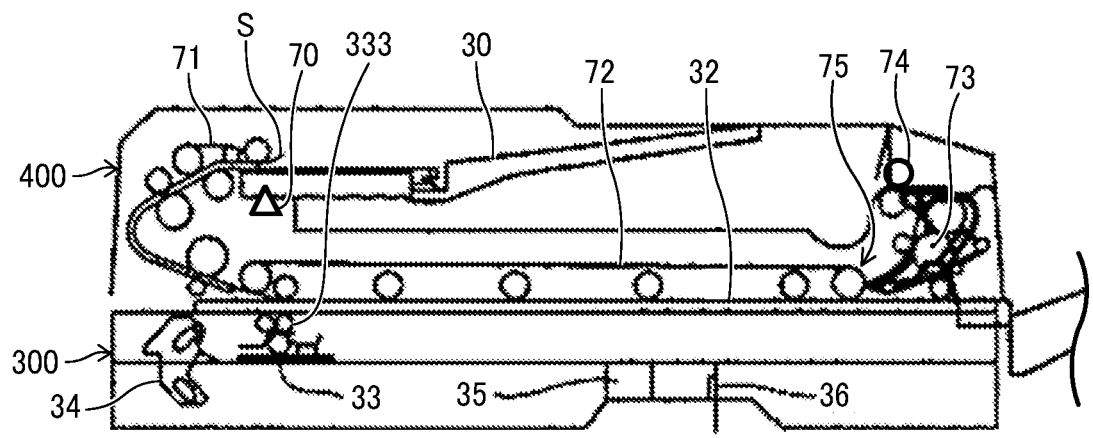
FIG. 2A, FIG. 2B, and FIG. 2C are diagrams each illustrating the color image forming apparatus of FIG. 1.

FIG. 2A is a magnified view of the image reading device 300 and the automatic document feeder (ADF) 400.

In the present embodiment described with reference to FIG. 1, the sheet feeding mechanism is provided with, for example, a document sensor 70, a feeding belt 71, a conveyance belt 72, a sheet-ejection drive roller 73, an output roller pair 74, and a switchback path 75.

In the present embodiment, duplex scanning is enabled as follows. The conveyance belt 72 stops the document on the contact glass 32, and the surface of the document that faces the contact glass is scanned. Then, the document is turned over and reversed such that the other side of the document will face the contact glass 32. As a result, the rear side of the document can be scanned. For this reason, a conveyance path switching claw is disposed around the sheet-ejection drive roller 73, and a conveyance roller that rotates in both forward and reverse directions and switches between entering and exiting from the switchback path 75 is also arranged.

The conveyance belt 72 is moved in the reverse feed direction as necessary. A structure different from the structure illustrated in the drawings may also be adopted as the duplex scanning mechanism.

Figure 2B:
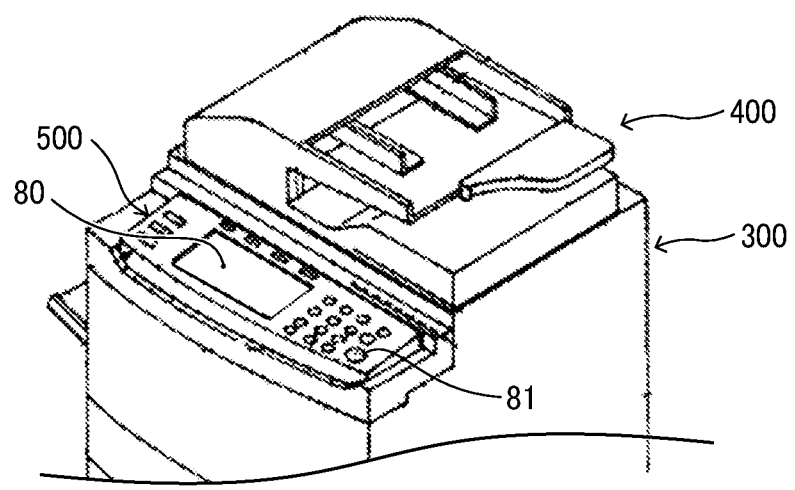

FIG. 2B is a perspective view of a control panel 500 according to the present embodiment.

The control panel 500 is provided with, for example, an operation panel 80 and a start key 81.

An image-forming operation is described below. Photocopying is performed using a color electrophotographic apparatus as follows. Firstly, when a document is set on a sheet tray 30, the document is detected by the document sensor 70. When the document on the sheet tray 30 is detected, the image reading device 300 enters a standby mode in which the image reading device 300 can start the operation. When the start key 81 is touched or pressed down in such a standby mode, the document conveyance operation is started.

Alternatively, photocopying is performed using a color electrophotographic apparatus as follows. Firstly, the automatic document feeder (ADF) 400 is opened to set a document on the contact glass 32 of the image reading device 300, and the automatic document feeder 400 is closed to hold the document by its platen. The automatic document feeder (ADF) 400 serves as a lid that can be opened and closed over the contact glass 32 that serves as a document placement plate. When a document is set on the automatic document feeder 400 and the start key 81 is touched or pressed down, the image reading device 300 is driven to run the first carrier 33 and the second carrier 34 after the document is conveyed and moved to the contact glass 32. On the other hand, when a document is set on the contact glass 32, the image reading device 300 is immediately driven to run the first carrier 33 and the second carrier 34.

Then, the light is emitted from a light-source lamp 333 provided for the first carrier 33, and the light that is reflected from the document surface is further reflected and directed to the second carrier 34. Then, the light is reflected by a mirror of the second carrier 34, and the reflected light enters the sensor 36 through the imaging lens 35. As a result, the image of the document is read and obtained.

When a start key 81 is touched or pressed down, one of supporting rollers 14, 15 and 16 is driven to rotate by a driving motor, the other two supporting rollers are driven to rotate, and an intermediate transferor 50 is rotated and carried. At the same time, the photoconductor 10 of each one of the multiple image forming devices 18 is driven to rotate to form a single-color image of yellow (Y), cyan (C), magenta (M), and black (BK) on the multiple photoconductors 10. Then, as the intermediate transferor 50 is conveyed, these multiple single-color images are sequentially transferred to form a composite color image on the intermediate transferor 50.

In the sheet feeding table 200, once the start key 81 is touched or pressed down, one of the sheet feeding rollers 42 is selectively rotated to feed a recording medium from one of the feed trays 44 vertically arranged in layers in the sheet bank 43, and the separation roller pair 45 separates a sheet from the stack of recording media in the feed tray 44 on a one-piece-by-one-piece basis to feed the sheet to the sheet conveyance path 46. The sheet is conveyed in the sheet conveyance path 46 and guided by conveyance rollers 47 to a sheet conveyance path 48 inside the photocopier housing 150, and the sheet stops moving when the sheet contacts a registration roller pair 49. Then, the registration roller pair 49 is rotated according to the timing of the composite color image on the intermediate transferor 50, and the sheet is fed between the intermediate transferor 50 and the secondary transfer device 22. Then, the color image is transferred by the secondary transfer device 22 to be recorded on the sheet.

The sheet on which the image has been transferred is conveyed by the secondary transfer device 22 and sent to the fixing device 25, and the fixing device 25 applies heat and pressure to the sheet to fix the transferred image. Then, the sheet is switched by a switching claw 55, and ejected by an output roller pair 56. The ejected sheets are stacked on top of each other in the output tray 57. Alternatively, the sheet is switched by the switching claw 55 so as to enter the sheet reversing device 28 and be reversed there. Then, the sheet is guided to the transfer position again, and an image is recorded on the rear side. Finally, the sheet is ejected onto the output tray 57 by the output roller pair 56.

On the other hand, the intermediate transferor cleaner 17 removes the residual toner remaining on the intermediate transferor 50 after image transfer is done, and the intermediate transferor 50 that has done the image transfer gets prepared for image formation to be performed again by the tandem image forming unit 20.

In the present embodiment given below, means for sterilization that sterilizes a document is described. In order to sterilize a document without a function of document conveyance when the document is being scanned by the image reading device 300 having the function of document conveyance, a sterilizing-light emitting light source is used as the light-source lamp 333 that is a light source to irradiate the document with light. As the sterilizing-light emitting light source, a UV-C lamp that serves as a light-source lamp having wavelength less than 280 nanometers (nm) may be used. This provides a highly effective ultraviolet sterilization. More preferably, a UV-C lamp with wavelength of 254 nm is used. This provides the most effective ultraviolet sterilization. Alternatively, a UV-C lamp with wavelength of 222 nm may also be used. This provides an effective ultraviolet sterilization effect, and does not affect the human body. In other words, the sterilization with the above lamp is safe to the human body.

More specifically, it is preferable to select, for example, a mercury lamp, a xenon lamp, or other fluorescent lamps as the light-source lamp that emits light having a wavelength in the ultraviolet region. In particular, a mercury lamp that can secure a sufficient radiation intensity of light in the ultraviolet region is suitable. Alternatively, an ultraviolet (UV) light-emitting diode (LED) or an excimer lamp can also be used.

As illustrated in FIG. 2A, such a light-source lamp 333 is disposed on the first carrier 33. The degree of irradiation of ultraviolet rays decreases as the distance from the light-source lamp 333 increases. For this reason, it is desired that the distance from the contact glass 32 be short as much as possible.

When an image on, for example, a document that can be conveyed by the automatic document feeder 400 is to be scanned, the image reading device 300 is stopped at a scanning position as illustrated in FIG. 2A facing the contact glass 32, and the image on the document that is being conveyed on the contact glass 32 is scanned and obtained. The document is irradiated with ultraviolet rays at least until the rear end of the document passes through an irradiation position where the light-source lamp 333 irradiates ultraviolet rays.

When the image on, for example, a document that cannot be conveyed by the automatic document feeder 400 is to be scanned, the light-source lamp 333 that is arranged on the first carrier 33 irradiates the contact glass 32 with ultraviolet (UV) light while moving from the left end to the right end of the sheet tray by the movement of the first carrier 33. The ultraviolet light that is emitted from the light-source lamp 333 passes through the contact glass 32, and irradiates the document from the left end to the right end of the document.

When there is a risk that ultraviolet light leaks outside the apparatus and affect the human body in an unintentional manner, preferably, a light-source lamp having wavelength of 222 nm that do not affect the human body is used as the light-source lamp 333. For example, when a thick document such as a book is set on the contact glass 32 and the automatic document feeder 400 is closed and pressed down, there is a risk that a gap is formed and the ultraviolet light leaks outside the apparatus in an unintentional manner. By contrast, when the automatic document feeder 400 is opened to set a document on the contact glass 32 of the image reading device 300 and the automatic document feeder 400 is closed to hold the document by its platen in an appropriate manner, the ultraviolet light that is emitted from the light-source lamp 333 does not leak outside the apparatus through the gap or the like.

When the rear side of the document on the other side of the document to be scanned is to be sterilized with ultraviolet (UV) light, in addition to a single-sided scanning operation mode and a duplex-scanning operation mode, a sterilization mode is prepared that is an operation mode in which image reading is performed on one side of the document and irradiation by the sterilizing-light emitting light source is performed but image reading is not performed on the other side of the document. In such an embodiment, a reading device is arranged only on one side. The document or sheet is set on the automatic document feeder 400, and the same operation as the duplexing reading operation by the automatic document feeder 400 is performed. By so doing, a side of the document with image and the rear side of the document can be simultaneously sterilized at once.

While the document or sheet is being sterilized, the light-source lamp 333 emits light. However, ultraviolet light is invisible to human eyes. In order to deal with such a situation, preferably, warning such as "Document is being sterilized" is displayed on the operation panel 80 in order to gain the recognition of a user. Alternatively, it is desired that the color on the operation panel 80 be turned to, for example, red in order to warn the user.

In addition to or in place of the above document sterilization, a sterilizing-light emitting light source may be arranged in the sheet conveyance path in the housing of the image forming apparatus 100. Preferably, the sterilizing-light emitting light source is arranged at a position where the sheet fed from the feed tray 44 is irradiated with light. The feed tray according to the present embodiment serves as a sheet container. The sterilizing-light emitting light source may be arranged directly onto the feed tray that is attachable to and detachable from the housing of the image forming apparatus.

Figure 2C:
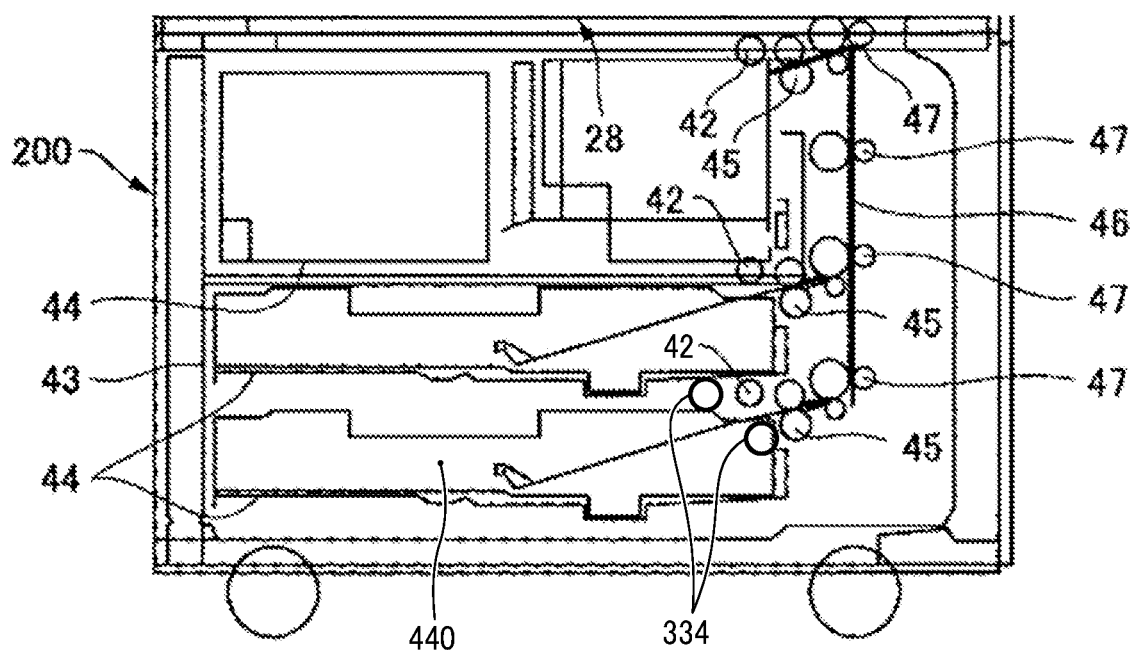

FIG. 2C is a diagram illustrating a sheet feeder in which a pair of light-source lamps 334 are provided for one of the multiple feed trays 44 in a lower layer to make up a tray 440 with a sterilizing function to sterilize sheet-like printing paper, according to the present embodiment.

The tray 440 with a sterilizing function may be replaced with a standard feed tray 44 that is equivalent to the feed tray 44 set in the middle. When a user wishes to use sterilized sheet, as illustrated in FIG. 2C, the standard tray 440 can be easily replaced with the tray 440 with a sterilizing function.

The tray 440 with a sterilizing function is provided with the pair of light-source lamps 334 in order to sterilize the printing paper. The lower one of the pair of light-source lamps 334 that is supported by the tray 440 with a sterilizing function is arranged near the sheet feeding roller 42 so as to irradiate the sheet with light from both the upper and lower sides with the other one of the pair of light-source lamps 334. The upper one of the pair of light-source lamps 334 is supported by the housing of the sheet feeder. The pair of light-source lamps 334 irradiate the sheet with light in conjunction with the sheet feeding and sheet conveyance operation of the printing paper. For this reason, the tray 440 with a sterilizing function is provided with a connector that receives supply of electric power from the sheet feeder and receives an on-off control signal as necessary.

Once the sheet feeding starts, the pair of light-source lamps 334 are turned on to irradiate the front end of the printing paper. As the sheet is conveyed upward, the entire sheet is evenly irradiated with light till the rear end of the sheet. When the rear end of the sheet passes, the light-source lamp 334 is turned off.

As the light-source lamp 334, a UV-C lamp with wavelength less than 280 nm that is effective for ultraviolet sterilization may be used. In particular, the use of wavelength of 254 nm is most effective for ultraviolet sterilization. As the light-source lamp 334 is arranged inside the sheet feeding table 200, when there is a few risk that ultraviolet light leaks outside the apparatus but there is a risk that the ultraviolet light may affect the human body in an unintentional manner, preferably, a light-source lamp having wavelength of 222 nm that do not affect the human body is used. In the case of the image forming apparatus 100 having both the document sterilizing function and the sheet sterilizing function, the most appropriate combination of lamps is as follows. That is the combination of the UV-C lamps with wavelength wider than 222 nm and the UV-C lamp with wavelength of 222 nm. The former is used for sheet sterilization, and used as the pair of light-source lamps 334. In particular, UV-C lamps with wavelength of 254 nm having the highest sterilization effect is desirable. The latter is used in the image reading device 300 provided with a placement plate on which a document is placed and a lid openable and closable over the placement plate.

As described above, in the present embodiment, the light-source lamps are used as the light source to irradiate the document with light when the document is to be scanned by the image reading device. Due to the adoption of such a configuration as described above, the document or sheet can be always sterilized during the document reading operation regardless of whether the document or sheet is photocopied using the automatic document feeder 400 or the sheet tray 30. Moreover, for example, a book or magazine other than the printing paper can also be sterilized. What is more, the printing paper or the like is stored in the tray with a sterilizing function that serves as the feed tray 44. Accordingly, bacteria and viruses can be prevented from adhering to the printing paper. In addition to or in place of the tray used for sterilizing the sheet or document, a sterilizing-light emitting light source may be arranged in the sheet conveyance path downstream from the feed tray. Note that numerous additional modifications and variations are possible in light of the above teachings. It is therefore to be understood that within the scope of the appended claims, the embodiments of the present disclosure may be practiced otherwise than as specifically described herein. For example, elements and/or features of different illustrative embodiments may be combined with each other and/or substituted for each other within the scope of this disclosure and appended claims.

Any one of the above-described operations may be performed in various other ways, for example, in an order different from the one described above.

Each of the functions of the described embodiments may be implemented by one or more processing circuits or circuitry. Processing circuitry includes a programmed processor, as a processor includes circuitry. A processing circuit also includes devices such as an application specific integrated circuit (ASIC), digital signal processor (DSP), field programmable gate array (FPGA), and conventional circuit components arranged to perform the recited functions.

What is claimed is:

1. An image reading device comprising
a light source configured to irradiate a sheet with light, the light source being a sterilizing-light emitting light source configured to irradiate the sheet with light to sterilize the sheet and configured to illuminate the sheet when reading an image on the sheet during scanning;
a display panel configured to present a warning message to a user indicating the light source is presently irradiating the sheet; and
a sheet conveyance device configured to enable duplex scanning, the sheet conveyance device having, in addition to a single-sided scanning operation mode and a duplex-scanning operation mode, an operation mode in which the sheet is conveyed in the same manner as in duplex-scanning operation mode, image reading and irradiation by the sterilizing-light emitting light source is performed on one side of the sheet, and irradiation by the sterilizing-light emitting light source is performed but image reading is not performed on another side of the sheet,
wherein the light source is configured to operate in a fixed position when the sheet is moving and is configured to operate while moving when the sheet is stationary.

2. The image reading device according to claim 1,
wherein the sterilizing-light emitting light source is a UV-C lamp with wavelength less than 280 nm.

3. The image reading device according to claim 2,
wherein the sterilizing-light emitting light source is a UV-C lamp with wavelength of 254 nm.

4. The image reading device according to claim 2,
wherein the sterilizing-light emitting light source is a UV-C lamp with wavelength of 222 nm.

* * * * *